United States Patent [19]

D'Amico

[11] 4,308,052
[45] Dec. 29, 1981

[54] N-SUBSTITUTED BENZOTHIAZOLINES SUBSTITUTED WITH THIOL ESTERS USEFUL AS HERBICIDES AND PLANT GROWTH REGULATORS

[75] Inventor: John J. D'Amico, St. Louis, Mo.

[73] Assignee: Monsanto Company, St. Louis, Mo.

[21] Appl. No.: 835,129

[22] Filed: Sep. 21, 1977

[51] Int. Cl.$^3$ .................... A01N 43/78; C07D 277/68
[52] U.S. Cl. .......................................... 71/90; 71/76; 546/157; 548/159; 548/170
[58] Field of Search ......... 260/283 S, 304 R, 287 CE; 71/76, 90; 546/157; 711/76, 90; 548/159, 170

[56] References Cited

U.S. PATENT DOCUMENTS

| 3,069,429 | 12/1962 | Godson et al. | 260/304 R |
|---|---|---|---|
| 3,864,117 | 2/1975 | Gante et al. | 71/115 |
| 3,873,301 | 3/1975 | O'Brien et al. | 71/106 |
| 3,954,442 | 5/1976 | Becker et al. | 71/108 |
| 3,989,710 | 11/1976 | Sasse et al. | 260/302 H |
| 3,993,468 | 11/1976 | D'Amico | 71/90 |
| 4,048,217 | 9/1977 | Rohr | 560/20 |
| 4,049,419 | 9/1977 | D'Amico | 71/76 |

FOREIGN PATENT DOCUMENTS 46-21378  6/1971  Japan .
48-10182  3/1973  Japan .

Primary Examiner—Donald G. Daus
Assistant Examiner—Diana G. Rivers
Attorney, Agent, or Firm—Richard H. Shear; Donald W. Peterson

[57] ABSTRACT

N-substituted benzothiazolines have been found to be effective herbicides and plant growth regulants. Said benzothiazolines are substituted with thiol esters.

14 Claims, No Drawings

N-SUBSTITUTED BENZOTHIAZOLINES SUBSTITUTED WITH THIOL ESTERS USEFUL AS HERBICIDES AND PLANT GROWTH REGULANTS

The invention relates to novel N-substituted benzothiazoline compounds. More particularly, the present invention is directed to N-substituted benzothiazolines having the formula

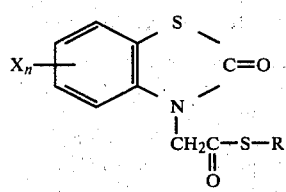

wherein R is selected from the group consisting of alkyl having from one to five carbon atoms; alkenyl having up to five carbon atoms; hydroxyalkyl having from one to five carbon atoms; haloalkyl having from one to five carbon atoms; haloalkenyl having up to five carbon atoms; benzyl, quinolyl and

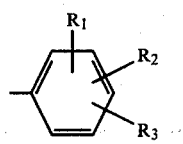

wherein $R_1$ and $R_2$ are independently selected from the group consisting of hydrogen and halo; $R_3$ is selected from the group consisting of hydrogen, halo, amino, nitro, trifluoromethyl, alkyl having from one to three carbon atoms, alkoxy having from one to three carbon atoms, phthalimido and $COOR_4$; $R_4$ is hydrogen or alkyl having from one to five carbon atoms; X is halo, and n is zero or one.

Preferred are those compounds in which n is zero.

Generally, the N-substituted benzothiazolines of the invention may be prepared in accordance with the following reaction:

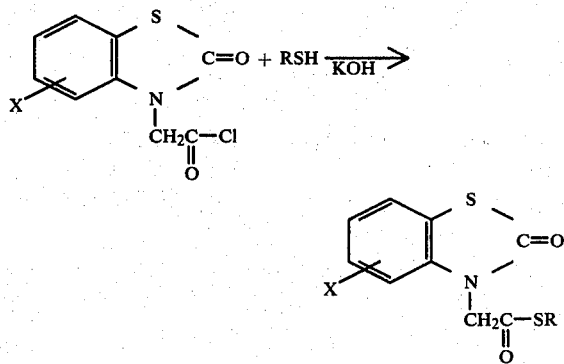

2-Oxo-3-benzothiazolineacetyl chloride may be prepared by adding an excess of a chlorinating agent, e.g., thionyl chloride, to 2-oxo-3-benzothiazolineacetic acid dissolved in benzene.

As illustrated above, the appropriate mercaptan, potassium hydroxide and a solvent, e.g., acetone or tetrahydrofuran, are stirred for a short period of time. To this stirred mixture is added a stoichiometric equivalent of 2-oxo-3-benzothiazolineacetyl chloride or a halogenated 2-oxo-3-benzothiazolineacetyl chloride.

The following examples are presented as an illustration of the matter in which the novel compounds of this invention can be prepared.

EXAMPLE 1

Preparation of S-(2'-Quinolinyl) 2-Oxo-3-Benzothiazolineethanethioate

A charge containing 0.1 moles of 2-mercaptoquinoline, 0.1 moles of 85% potasssium hydroxide and 250 ml of acetone is stirred for 10 minutes. To this stirred mixture is added 0.1 to 2-oxo-3-benzothiazolineacetyl chloride in one portion. An exothermic reaction set in causing a temperature rise from 30° C. to about 40° C. After stirring at room temperature for about 24 hours, 800 grams of cold water is added and stirring continued at 0°–10° C. for about 1 hour. The solid is then collected by filtration, washed with water until neutral to litmus and air-dried at 25°–30° C. Analytical data is summarized in Table I, below.

EXAMPLE 2

Preparation of S-(o-Aminophenyl) 2-Oxo-3-Benzothiazolineethanethioate

The procedure of Example 1 was repeated utilizing o-aminobenzenethiol as the reactant in lieu of 2-mercaptoquinoline and tetrahydrofuran in lieu of acetone. Analytical data is summarized in Table I, below.

EXAMPLE 3

Preparation of S-phenyl 5-Chloro-2-Oxo-3-Benzothiazolineethanethioate

A charge containing 0.1 moles of benzenethiol, 0.1 moles of 85% potassium hydroxide and 250 ml of acetone is stirred as in Example 1. To this mixture, 0.1 moles of 5-chloro-2-oxo-3-benzothiazolineacetyl chloride is added in one portion. The remaining steps of Example 1 are then followed. Analytical data is summarized in Table I, below.

EXAMPLE 4

Preparation of S-phenyl 2-Oxo-3-Benzothiazolineethanethioate

The procedure of Example 3 was followed utilizing 2-oxo-3-benzothiazolineacetyl chloride in lieu of 5-chloro-2-oxo-3-benzothiazolineacetyl chloride.

Utilizing the procedure of Example 4, the following compounds were prepared. Analytical data may be found in Table I, below.

| Example | Reactant | Reactant | Product |
|---|---|---|---|
| 5 | p-chlorobenzenethiol | 2-oxo-3-benzothiazolineacetyl chloride | S-(p-chlorophenyl) 2-oxo-3-benzothiazolineethanethioate |
| 6 | 2,4,5-trichlorobenzenethiol | 2-oxo-3-benzothiazolineacetyl chloride | S-(2,4,5-trichlorophenyl) 2-oxo-3-benzothiazolineethanethioate |
| 7 | m-phthalimidobenzenethiol | 2-oxo-3-benzothiazolineacetyl chloride | S-[(m-phthalimido(phenyl)] 2-oxo-3-benzothiazolineethanethioate |

| Example | Reactant | Reactant | Product |
|---|---|---|---|
| 8 | p-phthalimido-benzothiol | 2-oxo-3-benzo-thiazoline-acetyl chloride | S-[p-phthalimido(phenyl)] 2-oxo-3-benzothiazoline-ethanethioate |
| 9 | 2-mercapto-methylbenzoate | 2-oxo-3-benzo-thiazoline-acetyl chloride | 2-mercapto-methylbenzoate ester of 2-oxo-3-benzothiazoline-ethanethioic acid |
| 10 | benzylthiol | 2-oxo-3-benzo-thiazoline-acetyl chloride | S-benzyl 2-oxo-3-benzothia-zolineethane-thioate |
| 11 | ethylthiol | 2-oxo-3-benzo-thiazoline-acetyl chloride | S-ethyl 2-oxo-3-benzothia-zolineethane-thioate |
| 12 | n-propylthiol | 2-oxo-3-benzo-thiazoline-acetyl chloride | S-n-propyl 2-oxo-3-benzo-thiazoline-ethanethioate |
| 13 | isopropylthiol | 2-oxo-3-benzo-thiazoline-acetyl chloride | S-isopropyl 2-oxo-3-benzo-thiazoline-ethanethioate |
| 14 | tert. butylthiol | 2-oxo-3-benzo-thiazoline-acetyl chloride | S-tert. butyl 2-oxo-3-benzo-thiazoline-ethanethioate |
| 15 | allylthiol | 2-oxo-3-benzo-thiazoline-acetyl chloride | S-allyl 2-oxo-3-benzothia-zolineethane-thioate |

EXAMPLE 16

Preparation of S-(2-Hydroxyethyl) 2-Oxo-3-Benzothiazolineethanethioate

A charge containing 0.1 moles of mercaptoethanol, 0.1 moles of 85% potassium hydroxide and 250 ml of acetone is stirred for 10 minutes. To this stirred mixture is added 0.1 moles of 2-oxo-3-benzothiazolineacetyl chloride in one portion. An exothermic reaction set in causing a temperature rise from 30° to about 40° C. After stirring for about 24 hours at room temperature, 500 ml of water and 500 ml of ethyl ether are added and stirring continued at 25°–30° C. for 15 minutes. The separated ether layer is washed with water until neutral to litmus and dried over sodium sulfate. The ether is removed in vacuo at a maximum temperature of 80°–90° C. at 1–2 minutes. Analytical data is summarized in Table I, below.

TABLE I

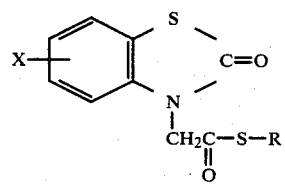

| Ex. No. | X | R | MP °C. | Yield % | % C Calc'd. | % C Found | % H Calc'd. | % H Found | % N Calc'd. | % N Found | % S Calc'd. | % S Found |
|---|---|---|---|---|---|---|---|---|---|---|---|---|
| 1 | H | quinolinyl | 99–100 | 74 | 61.34 | 61.07 | 3.43 | 3.54 | 7.95 | 8.04 | 18.20 | 18.26 |
| 2 | H | H₂N–phenyl | 167–9 | 72 | 56.94 | 57.12 | 3.82 | 3.86 | 8.85 | 8.94 | 20.27 | 20.41 |
| 3 | Cl | phenyl | 137–9(a)(f) | 82 | — | — | — | — | 4.17 | 4.38 | — | — |
| 4 | H | phenyl | 120–2 | 67 | 59.78 | 59.74 | 3.68 | 3.72 | 4.65 | 4.63 | 21.28 | 21.35 |
| 5 | H | p-Cl-phenyl | 138–9(b) | 80 | 53.60 | 53.71 | 3.00 | 3.04 | 4.17 | 4.20 | 19.10 | 19.11 |
| 6 | H Cl | trichlorophenyl | 169–70(c) | 86 | 44.52 | 43.75 | 1.99 | 1.95 | 3.46 | 3.39 | 15.84 | 15.57 |
| 7 | H | phthalimido-phenyl | 157–8 | 67 | 61.87 | 62.37 | 3.16 | 3.38 | 6.27 | 5.87 | 14.36 | 14.39 |

TABLE I-continued

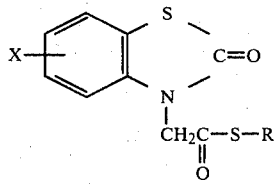

| Ex. No. | X | R | MP °C. | Yield % | % C Calc'd. | % C Found | % H Calc'd. | % H Found | % N Calc'd. | % N Found | % S Calc'd. | % S Found |
|---|---|---|---|---|---|---|---|---|---|---|---|---|
| 8 | H | (phthalimidophenyl group) | 191–3 | 74 | 61.87 | 62.56 | 3.16 | 3.32 | 6.27 | 5.91 | 14.36 | 13.78 |
| 9 | H | —C(=O)OCH₃ (phenyl) | 114–5[d] | 76 | 56.81 | 56.89 | 3.65 | 3.81 | 3.90 | 3.54 | — | — |
| 10 | H | —CH₂—(phenyl) | 112–3[d] | 79 | 60.93 | 60.83 | 4.15 | 4.39 | 4.44 | 4.26 | 20.33 | 20.36 |
| 11 | H | —C₂H₅ | 112–3[e] | 63 | 52.15 | 52.10 | 4.38 | 4.42 | 5.53 | 5.56 | 25.31 | 25.19 |
| 12 | H | —C₃H₇ | 80–1[e] | 52 | 53.91 | 53.96 | 4.90 | 4.90 | 5.24 | 5.29 | 23.98 | 23.98 |
| 13 | H | —CH(CH₃)₂ | 56–7 | 37 | 53.91 | 53.98 | 4.90 | 4.93 | 5.24 | 5.24 | 23.98 | 23.86 |
| 14 | H | —C(CH₃)₃ | 90–1[e] | 46 | 55.49 | 55.52 | 5.37 | 5.38 | 4.98 | 5.00 | 22.79 | 22.62 |
| 15 | H | —CH₂CH=CH₂ | 93–5[c] | 42 | 54.32 | 54.08 | 4.18 | 4.24 | 5.28 | 5.14 | 24.17 | 24.02 |
| 16 | H | —CH₂CH₂OH | viscous liquid | 43 | 49.05 | 48.41 | 4.12 | 4.01 | 5.20 | 5.12 | 23.81 | 24.36 |

[a]Recrystallization from ethyl acetate
[b]Recrystallization from methyl alcohol
[c]Recrystallization from toluene
[d]Recrystallization from isopropyl alcohol
[e]Recrystallization from heptane/isopropyl alcohol
[f]Calc'd., Cl - 4.17; Found, Cl - 4.38

EXAMPLE 17

Preparation of S-(o-Carboxyphenyl) 2-Oxo-3-Benzothiazolineethanethioate

A charge containing 0.1 moles of o-thiosalicylic acid, 0.2 moles of 85% potassium hydroxide, 200 ml of dimethylformamide and 10 ml of water is stirred for 10 minutes. To this stirred solution at 30° C., is added 0.1 moles of 2-oxo-3-benzothiazolineacetyl chloride. An exothermic reaction set in causing a temperature rise from 30° to 47° C. After stirring at room temperature for 24 hours, 700 ml of water and 20 grams of concentrated hydrochloric acid are added. The reaction mixture is stirred at 0° to 10° C. for 2 hours. The solid is collected by filtration, washed with water until neutral to litmus and air-dried at room temperature. The product, mp 161°–3° C., was obtained in 61% yield.

Anal. Calc'd for $C_{16}H_{11}NO_4S_2 \cdot H_2O$: C, 52.88; H, 3.61; N, 3.85; S, 17.65.

Found: C, 52.88; H, 3.75; N, 3.38; S, 17.86.

EXAMPLE 18

Preparation of S-Methyl 2-Oxo-3-Benzothiazolineethanethioate

S-methyl 2-oxo-3-benzothiazolineethanethioate may be prepared in accordance with the procedure of Example 1 by replacing mercaptoquinoline by methylthiol. S-methyl 2-oxo-3-benzothiazolineethanethioate has a melting point of 146°–7° C.

The N-substituted benzothiazoline compounds of the foregoing formula have been found to be herbicidally effective in controlling the growth of undesired vegetation. The compounds have been found to be herbicidally effective when applied to the soil in what is known in the art as a pre-emergent treatment. They have further been found to be herbicidally effective when applied foliarly to the plants in what is known as a post-emergent treatment.

As used herein, the term "active ingredient" is understood to mean an N-substituted benzothiazoline of the foregoing formula.

To illustrate the herbicidal properties of the N-substituted benzothiazolines, said compounds were tested in the following manner.

The pre-emergent test was conducted as follows.

A good grade of top soil was placed in aluminum pans and compacted to a depth of three-eighths to one-half inch from the top of the pan. On the top of the soil was placed a predetermined number of seeds or vegetative propagules of various plant species. The soil required to level fill the pans after seeding or adding vegetative propagules was weighed into a pan. A known amount of the active ingredient applied in a solvent or as a wettable powder and the soil were thoroughly mixed, and used as a cover layer for prepared pans. After treatment the pans were moved into a greenhouse bench where they were watered from below as needed to give adequate moisture for germination and growth.

Unless noted otherwise, approximately 28 days after seeding and treating, the plants were observed to determine all deviations from the normal growth habit and the results recorded. A herbicidal rating code was used to signify the extent of phytotoxicity of each species. The ratings are defined as follows:

| % Control | Rating |
|---|---|
| 0-24 | 0 |
| 25-49 | 1 |
| 50-74 | 2 |
| 75-100 | 3 |

The plant species utilized in these tests are identified by letter in accordance with the following legend:

| | |
|---|---|
| A - Canada Thistle | K - Barnyard Grass |
| B - Cocklebur | L - Soybean |
| C - Velvetleaf | M - Sugar Beet |
| D - Morning Glory | N - Wheat |
| E - Lambsquarters | O - Rice |
| F - Smartweed | P - Sorghum |
| G - Nutsedge | Q - Wild Buckwheat |
| H - Quackgrass | R - Hemp Sesbania |
| I - Johnson Grass | S - Panicum Spp |
| J - Downy Brome | T - Crabgrass |

Results of the pre-emergent tests are summarized in Tables II and III, below.

TABLE II

| Compound | kg h | A | B | C | D | E | F | G | H | I | J | K |
|---|---|---|---|---|---|---|---|---|---|---|---|---|
| 1 | 11.2 | 3 | 1 | 1 | 1 | 2 | 2 | 0 | 1 | 0 | 0 | 1 |
| 2* | 11.2 | 1 | 1 | 0 | 0 | 0 | 0 | 0 | 0 | 0 | 0 | 1 |
| 3 | 11.2 | 1 | 2 | 1 | 2 | 2 | 2 | 0 | 0 | 0 | 0 | 0 |
| 4 | 5.6 | 3 | 2 | 2 | 1 | 3 | 1 | 0 | 0 | 0 | 0 | 0 |
| 5* | 5.6 | 2 | 1 | 0 | 1 | 0 | 1 | 0 | 0 | 0 | 0 | 0 |
| 6 | 11.2 | 3 | 1 | 1 | 1 | 3 | 2 | 0 | 0 | 0 | 0 | 0 |
| 7 | 11.2 | 3 | 1 | 1 | 1 | 2 | 1 | 0 | 0 | 0 | 0 | 0 |
| 8 | 11.2 | 3 | 1 | 1 | 1 | 2 | 1 | 0 | 0 | 0 | 0 | 0 |
| 9 | 5.6 | 3 | 2 | 2 | 2 | 3 | 2 | 0 | 2 | 0 | 1 | 0 |
| 10 | 5.6 | 2 | 1 | 1 | 1 | 3 | 2 | 0 | 0 | 0 | 0 | 0 |
| 11 | 11.2 | 3 | 2 | 3 | 3 | 3 | 3 | 0 | 2 | 1 | 1 | 3 |
| 12 | 11.2 | 3 | 3 | 3 | 2 | 3 | 3 | 0 | 3 | 2 | 0 | 3 |
| 13 | 5.6 | 3 | 2 | 2 | 2 | 3 | 2 | 0 | 1 | 0 | 1 | 1 |
| 14 | 5.6 | 3 | 2 | 2 | 2 | 3 | 2 | 0 | 3 | 0 | 2 | 1 |
| 15 | 5.6 | 3 | 2 | 1 | 1 | 3 | 1 | 0 | 1 | 0 | 0 | 1 |
| 16* | 5.6 | 0 | 1 | 1 | 0 | 2 | 0 | 0 | 0 | 0 | 0 | 0 |
| 17* | 5.6 | 2 | 0 | 0 | 0 | 1 | 1 | 0 | 0 | 0 | 0 | 0 |
| 18 | 5.6 | 3 | 1 | 1 | 1 | 2 | 1 | 0 | 1 | 0 | 0 | 0 |

*plants observed 14 days after treatment

TABLE III

| Compound | kg h | L | M | N | O | P | B | Q | D | R | E | F | C | J | S | K | T |
|---|---|---|---|---|---|---|---|---|---|---|---|---|---|---|---|---|---|
| 4 | 5.6 | 3 | 2 | 0 | 0 | 0 | 2 | 1 | 1 | 2 | 3 | 2 | 1 | 0 | 0 | 0 | 1 |
| 4 | 1.12 | 1 | 0 | 0 | 0 | 0 | 1 | 1 | 1 | 1 | 2 | 0 | 1 | 0 | 0 | 0 | 0 |
| 6 | 5.6 | 2 | 1 | 0 | 0 | 0 | 1 | 1 | 1 | 2 | 2 | 2 | 1 | 0 | 0 | 0 | 0 |
| 6* | 1.12 | 1 | 0 | 0 | 0 | 0 | 0 | 0 | 0 | 0 | 0 | 0 | 0 | 0 | 0 | 0 | 0 |
| 11 | 5.6 | 3 | 3 | 1 | 0 | 0 | 3 | 3 | 3 | 3 | 3 | 3 | 2 | 1 | 1 | 2 | 1 |
| 11 | 1.12 | 2 | 2 | 0 | 0 | 0 | 1 | 1 | 1 | 1 | 1 | 1 | 1 | 0 | 1 | 1 | 0 |
| 11* | 0.28 | 1 | 0 | 0 | 0 | 0 | 1 | 0 | 0 | 0 | 0 | 0 | 0 | 0 | 0 | 0 | 0 |
| 12 | 5.6 | 3 | 2 | 1 | 1 | 0 | 2 | 2 | 2 | 3 | 3 | 2 | 1 | 1 | 1 | 3 | 3 |
| 12 | 1.12 | 2 | 2 | 0 | 0 | 0 | 1 | 1 | 1 | 1 | 2 | 1 | 1 | 0 | 0 | 0 | 0 |
| 12* | 0.28 | 1 | 0 | 0 | 0 | 0 | 1 | 0 | 0 | 1 | 0 | 0 | 0 | 0 | 0 | 0 | 0 |

*plants observed 14 days after treatment

The post-emergent tests were conducted as follows.

The active ingredients are applied in spray form to two or three-week old specimens of various plant species. The spray, a solution or wettable powder suspension containing the appropriate rate of active ingredient to give the desired test rate and a surfactant, is applied to the plants. The treated plants are placed in a greenhouse and unless otherwise noted approximately four weeks later the effects are observed and recorded. The results are shown in Tables IV and V in which the post-emergent herbicidal rating code is as follows:

| % Control | Rating |
|---|---|
| 0-24 | 0 |
| 25-49 | 1 |
| 50-74 | 2 |
| 75-99 | 3 |
| 100 | 4 |

The plant species utilized in these tests are identified by letter in accordance with the previous legend.

TABLE IV

| Compound | kg h | A | B | C | D | E | F | G | H | I | J | K |
|---|---|---|---|---|---|---|---|---|---|---|---|---|
| 1 | 11.2 | 2 | 4 | 1 | 1 | 4 | 4 | 0 | 0 | 0 | 0 | 0 |
| 2* | 11.2 | 0 | 1 | 1 | 0 | 0 | 0 | 0 | 0 | 0 | 0 | 0 |
| 3 | 11.2 | 1 | 2 | 2 | 3 | 4 | 2 | 0 | 0 | 0 | 0 | 0 |
| 4 | 5.6 | 2 | 2 | 2 | 2 | 4 | 1 | 0 | 0 | 0 | 0 | 0 |
| 5 | 5.6 | 2 | 2 | 1 | 2 | 3 | 1 | 0 | 0 | 0 | 0 | 0 |
| 6 | 11.2 | 1 | 2 | 1 | 2 | 2 | 1 | 0 | 0 | 0 | 0 | 0 |
| 7 | 11.2 | 1 | 2 | 1 | 1 | 2 | 1 | 0 | 0 | 0 | 0 | 0 |
| 8 | 11.2 | 1 | 1 | 1 | 1 | 1 | 0 | 0 | 0 | 0 | 0 | 0 |
| 9 | 5.6 | 3 | 3 | 2 | 2 | 4 | 3 | 0 | 0 | 0 | 0 | 0 |
| 10 | 5.6 | 2 | 1 | 1 | 1 | 2 | 1 | 0 | 0 | 0 | 0 | 0 |
| 11 | 11.2 | 3 | 4 | 2 | 2 | 4 | 4 | 0 | 0 | 0 | 0 | 0 |
| 11 | 5.6 | 4 | 3 | 2 | 2 | 3 | 3 | 0 | 0 | 1 | 0 | 0 |
| 12 | 11.2 | 3 | 4 | 2 | 2 | 4 | 4 | 0 | 0 | 0 | 0 | 0 |
| 12 | 5.6 | 2 | 3 | 2 | 2 | 3 | 3 | 0 | 1 | 1 | 0 | 0 |
| 13 | 5.6 | 2 | 3 | 3 | 2 | 4 | 4 | 0 | 1 | 0 | 0 | 0 |
| 14 | 5.6 | 2 | 2 | 1 | 1 | 3 | 1 | 0 | 0 | 0 | 0 | 0 |
| 15 | 5.6 | 1 | 3 | 2 | 2 | 4 | 1 | 0 | 0 | 0 | 0 | 0 |
| 16 | 5.6 | 4 | 4 | 3 | 2 | 4 | 4 | 0 | 0 | 1 | 0 | 0 |
| 17 | 5.6 | 4 | 2 | 2 | 2 | 4 | 2 | 0 | 0 | 0 | 0 | 0 |
| 18 | 5.6 | 2 | 2 | 2 | 2 | 3 | 2 | 0 | 0 | 0 | 0 | 0 |

*plants observed 14 days after treatment

TABLE V

| Compound | kg h | L | M | N | O | P | B | Q | D | R | E | F | C | J | S | K | T |
|---|---|---|---|---|---|---|---|---|---|---|---|---|---|---|---|---|---|
| 1 | 5.6 | 1 | 2 | 0 | 0 | 1 | 2 | 3 | 2 | 3 | 3 | 2 | 2 | 1 | 0 | 0 | 0 |
| 1 | 1.12 | 1 | 1 | 0 | 0 | 0 | 2 | 2 | 2 | 1 | 3 | 1 | 2 | 0 | 0 | 0 | 0 |
| 3 | 1.12 | 2 | 2 | 0 | 0 | 1 | 2 | 2 | 3 | 1 | 2 | 0 | 2 | 0 | 0 | 0 | 0 |

TABLE V-continued

| Com-pound | kg h | L | M | N | O | P | B | Q | D | R | E | F | C | J | S | K | T |
|---|---|---|---|---|---|---|---|---|---|---|---|---|---|---|---|---|---|
| 3 | 0.28 | 1 | 2 | 0 | 0 | 1 | 2 | 1 | 2 | 1 | 1 | 0 | 1 | 0 | 0 | 0 | 0 |
| 9 | 5.6 | 2 | 2 | 0 | 0 | 0 | 4 | 4 | 2 | 3 | 4 | 4 | 3 | 0 | 0 | 0 | 0 |
| 9 | 1.12 | 2 | 1 | 0 | 0 | 0 | 2 | 3 | 2 | 2 | 4 | 4 | 2 | 0 | 0 | 0 | 0 |
| 9 | 0.28 | 1 | 1 | 0 | 0 | 0 | 1 | 1 | 1 | 1 | 2 | 2 | 1 | 0 | 0 | 0 | 0 |
| 11* | 5.6 | 1 | 3 | 0 | 0 | 0 | 3 | 3 | 3 | 2 | 3 | 2 | 2 | 0 | 0 | 0 | 0 |
| 12 | 5.6 | 3 | 3 | 1 | 0 | 1 | 4 | 4 | 2 | 4 | 4 | 4 | 4 | 0 | 0 | 0 | 0 |
| 12 | 1.12 | 2 | 2 | 1 | 0 | 0 | 3 | 3 | 2 | 2 | 3 | 2 | 2 | 0 | 0 | 1 | 0 |
| 12 | 0.28 | 1 | 1 | 0 | 0 | 0 | 2 | 1 | 1 | 1 | 2 | 1 | 1 | 0 | 0 | 1 | 0 |
| 13 | 5.6 | 2 | 3 | 0 | 0 | 0 | 3 | 4 | 2 | 4 | 4 | 4 | 4 | 0 | 0 | 0 | 0 |
| 13 | 1.12 | 1 | 2 | 0 | 0 | 0 | 2 | 2 | 2 | 1 | 3 | 2 | 2 | 0 | 0 | 0 | 0 |
| 13* | 0.28 | 0 | 1 | 0 | 0 | 0 | 1 | 1 | 0 | 0 | 1 | 0 | 1 | 0 | 0 | 0 | 0 |
| 15 | 5.6 | 2 | 3 | 1 | 0 | 0 | 3 | 4 | 2 | 3 | 4 | 4 | 3 | 0 | 0 | 0 | 0 |
| 15 | 1.12 | 2 | 3 | 0 | 0 | 0 | 2 | 2 | 2 | 2 | 4 | 4 | 2 | 0 | 0 | 0 | 0 |
| 15 | 0.28 | 1 | 1 | 0 | 0 | 0 | 1 | 1 | 1 | 0 | 1 | 1 | 1 | 0 | 0 | 0 | 0 |
| 16 | 5.6 | 2 | 4 | 1 | 0 | 0 | 3 | 4 | 3 | 4 | 4 | 4 | 4 | 0 | 1 | 0 | 0 |
| 16 | 1.12 | 2 | 2 | 0 | 0 | 0 | 2 | 3 | 2 | 2 | 4 | 4 | 2 | 0 | 0 | 0 | 0 |
| 16 | 0.28 | 1 | 0 | 0 | 0 | 0 | 1 | 2 | 2 | 2 | 2 | 2 | 2 | 0 | 0 | 0 | 0 |
| 16* | .056 | 0 | 0 | 0 | 0 | 0 | 1 | 0 | 1 | 0 | 1 | 0 | 0 | 0 | 0 | 0 | 0 |

*plants observed 14 days after treatment

As can be seen from the above tables, the N-substituted benzothiazoline compounds of the invention possess significant herbicidal activity. They are especially effective in inhibiting the growth of broadleaf weeds. A review of the above data leads to the conclusion that the compounds of the invention may be applied to narrowleaf crops, such as wheat, rice and sorghum to selectively inhibit the growth of weeds, especially broadleaf weeds.

The compounds of the invention have also been found to be effective in regulating the growth of leguminous plants, such as soybeans.

As used herein, the regulation of "plant growth or development" is understood to mean the modification of the normal sequential development of a treated desirable plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color may be illustrative of higher chlorophyll activity indicative of improved rate of photosynthesis.

Although the regulation of plant growth in accordance with the present invention may include partial inhibition of plant growth, is does not include the total inhibition or killing of such plants. The present invention contemplates the use of an amount of active ingredient which will modify the normal sequential development of the treated plant to agricultural maturity. Such plant growth regulating amounts may vary, not with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to seeds, emerging seedlings, roots, stems, leaves, flowers, fruits or other plant parts. Such application may be made directly to the plant part, or indirectly by application to the plant growth medium.

Utilizing the N-substituted benzothiazolines as the active ingredient in a plant growth regulating composition, said compounds were found to possess plant growth regulating activity when tested in accordance with the following procedure.

A number of soybean plants, variety Williams, were grown from seeds in plastic pots in the greenhouse for a period of one week at which time the plants are thinned to one plant per pot. When the second trifoliate leaf (three weeks) was fully expanded, the plants were treated with a solution of the active ingredient in acetone and water. Aqueous Tween 20 was used as a surfactant.

When the fifth trifoliate leaf (four to five weeks) was fully expanded, the treated plants were compared with the non-treated control plants and the observations recorded. Results of these tests are summarized in Table VI, below.

TABLE VI

| Com-pound | Rate kg/ha | Dry Weight % of Control | Observations |
|---|---|---|---|
| 1 | 2.8 | 33 | Stature reduction, epinasty, leaf alteration, leaf inhibition, altered canopy, slight leaf burn |
| 1 | 0.56 | 42 | Stature reduction, stem distortion, leaf alteration, leaf inhibition, altered canopy |
| 1 | 0.112 | 67 | Leaf alteration, leaf inhibition, altered canopy |
| 4 | 2.8 | 24 | Stature reduction, epinasty, leaf distortion, altered canopy, slight leaf burn |
| 4 | 0.56 | 28 | Stature reduction, epinasty, leaf distortion, altered canopy, slight leaf burn |
| 4 | 0.112 | 73 | Stem distortion, leaf alteration, leaf inhibition |
| 7 | 2.8 | 42 | Stature reduction, chlorosis, stem distortion, leaf alteration, inhibition of apical development |
| 7 | 0.56 | 49 | Stature reduction, chlorosis, stem distortion, leaf alteration, inhibition of apical development |
| 7 | 0.112 | 78 | Leaf alteration, leaf inhi- |

TABLE VI-continued

| Compound | Rate kg/ha | Dry Weight % of Control | Observations |
|---|---|---|---|
| 11 | 6.72 | 40 | bition, altered canopy Stature reduction, epinasty, leaf distortion, leaf inhibition |
| 12 | 2.8 | 25 | Stature reduction, epinasty, leaf distortion, leaf inhibition, inhibition of apical development, moderate leaf burn |
| 12 | 0.56 | 42 | Stature reduction, epinasty, leaf distortion, leaf inhibition, inhibition of apical development, slight leaf burn |
| 12 | 0.112 | 62 | Stature reduction, epinasty, leaf inhibition, altered canopy, inhibition of apical development |
| 15 | 2.8 | 17 | Stature reduction, epinasty, leaf distortion, altered canopy, inhibition of apical development, moderate leaf burn |
| 15 | 0.56 | 30 | Stature reduction, stem distortion, leaf alteration, leaf inhibition, altered canopy |
| 15 | 0.112 | 73 | Stem distortion, leaf alteration, leaf inhibition, altered canopy |
| 16 | 2.8 | 23 | Stature reduction, epinasty, leaf alteration, leaf inhibition, altered canopy, slight leaf burn |
| 16 | 0.56 | 33 | Stature reduction, epinasty, leaf alteration, leaf inhibition, altered canopy |
| 16 | 0.112 | 56 | Stature reduction, stem distortion, leaf alteration, altered canopy, axillary bud inhibition |

The above data illustrate that the compounds of the invention may be used as a herbicide or a plant growth regulant. When used as a herbicide, it is desirable that rates of application above 2.24 kilograms per hectare be utilized. When used to regulate the growth of desirable plants, rates below 5.6 kilograms per hectare especially 0.056 to 3.36 are preferred.

In selecting the appropriate time and rate of application of the active ingredient, it will be recognized that precise rates will also be dependent upon the desired response, mode of application, plant variety, soil conditions and various other factors known to those skilled in the art. While a rate of about 0.056 to 5.6 kilos per hectare is preferred, higher rates of up to 56 kilos per hectare may be used, depending upon the factors noted above. In addition, it will be recognized that single or multiple applications may be used to exert the desired response.

When operating in accordance with the present invention, effective amounts of the active ingredients are applied to the plant system. By application to the plant system is meant the application of the active ingredient in or on soil or plant growth media and/or applied to above ground portions of plants in any convenient fashion. Application to the soil or growth media can be carried out by simply mixing with the soil, by applying to the surface of the soil and thereafter dragging or discing into the soil to the desired depth, or by employing a liquid carrier to accomplish the penetration and impregnation. The application of liquid and particulate solid herbicidal formulations to the surface of soil or to above ground portions of plants can be carried out by conventional methods, e.g. powder dusters, boom and hand sprayers and spray dusters. The formulations can also be applied from airplanes as a dust or a spray because of their effectiveness at low dosages. In a further method, the distribution of the active ingredients in soil can be carried out by admixture with the water employed to irrigate the soil. In such procedures, the amount of water can be varied with the porosity and water holding capacity of the soil to obtain the desired depth of distribution of the active ingredients.

As noted, the active ingredient can be used alone or in combination with other pesticides or a material referred to in the art as an adjuvant in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, Columns 3 and 4, for detailed examples of the same.

Compositions of this invention generally contain from about 1 to 99 parts active ingredient, about 1 to 50 parts surface-active agent and about 4 to 94 parts solvents, all parts being by weight based on the total weight of the composition.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

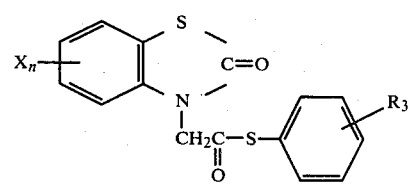

wherein $R_3$ is selected from the group consisting of phthalimido and $COOR_4$; $R_4$ is hydrogen or alkyl having from one to five carbon atoms; X is halo, and n is zero or one.

2. The compound of claim 1 which is S-[(m-phthalimido(phenyl)] 2-oxo-3-benzothiazolineethanethioate.

3. The compound of claim 1 which is S-[(p-phthalimido(phenyl)] 2-oxo-3-benzothiazolineethanethioate.

4. The compound which is S-(2'-quinolinyl) 2-oxo-3-benzothiazolineethanethioate.

5. A method for inhibiting the growth of undesirable plants which comprises applying to the plant system a herbicidally effective amount of a compound having the formula

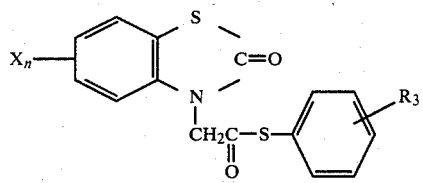

wherein $R_3$ is selected from the group consisting of phthalimido and $COOR_4$; $R_4$ is hydrogen or alkyl having from one to five carbon atoms; X is halo, and n is zero or one.

6. The method of claim 5 wherein the compound is S-[(m-phthalimido(phenyl)] 2-oxo-3-benzothiazolineethanethioate.

7. The method of claim 5 wherein said compound is S-[(p-phthalimido(phenyl)] 2-oxo-3-benzothiazolineethanethioate.

8. A method for regulating the growth of leguminous plants which comprises applying to the plant system an effective, non-lethal amount of a compound having the formula

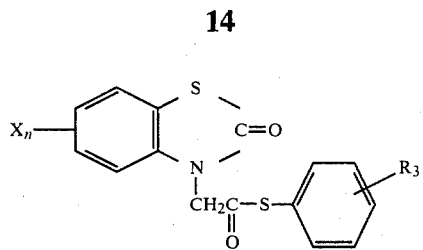

wherein $R_3$ is selected from the group consisting of phthalimido and $COOR_4$; $R_4$ is hydrogen or alkyl having from one to five carbon atoms; X is halo, and n is zero or one.

9. The method of claim 8 wherein said compound is S-[(m-phthalimido(phenyl)] 2-oxo-3-benzothiazolineethanethioate.

10. The method of claim 8 wherein said compound is S-[(p-phthalimido(phenyl)] 2-oxo-3-benzothiazolineethanethioate.

11. An agricultural chemical composition comprising from about 1 to about 99 parts by weight of a compound having the formula

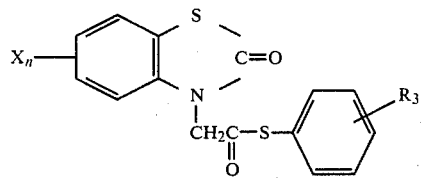

wherein $R_3$ is selected from the group consisting of phthalimido and $COOR_4$; $R_4$ is hydrogen or alkyl having from one to five carbon atoms; X is halo, and n is zero or one; the remaining parts being comprised of one or more suitable carriers, diluents and/or adjuvants.

12. The composition of claim 11 in which said compound is S-[(m-phthalimido(phenyl)] 2-oxo-3-benzothiazolineethanethioate.

13. The composition of claim 11 in which said compound is S-[(p-phthalimido(phenyl)] 2-oxo-3-benzothiazolineethanethioate.

14. An agricultural chemical composition comprising from about 1 to about 99 parts by weight of S-(2'-quinolinyl)-2-oxo-3-benzothiazolineethanethioate; the remaining parts being composed of one or more suitable carriers, diluents and/or adjuvants.

* * * * *